United States Patent [19]

Dreyer

[11] Patent Number: 5,075,215
[45] Date of Patent: Dec. 24, 1991

[54] USE OF DAYLIGHT FLUORESCENT PIGMENTS FOR TAGGING BIOLOGICAL MOLECULES

[76] Inventor: William J. Dreyer, 960 San Pasqual, #302, Pasadena, Calif. 91106

[21] Appl. No.: 710,375

[22] Filed: Jun. 3, 1991

Related U.S. Application Data

[62] Division of Ser. No. 262,184, Oct. 20, 1988.

[51] Int. Cl.⁵ .......................... C12Q 1/68; C12Q 1/00
[52] U.S. Cl. .......................................... 435/6; 435/4; 435/7.1; 435/91; 436/94; 436/501; 436/518; 436/523; 436/532; 436/800; 436/805; 436/810; 436/814; 436/818; 935/76; 935/78
[58] Field of Search ...................... 435/6, 803, 7.4, 91; 436/94, 501, 518, 523, 4, 800, 805, 809, 810, 818, 814; 422/61; 935/78, 81, 76

[56] References Cited

U.S. PATENT DOCUMENTS

| | | | |
|---|---|---|---|
| 2,809,954 | 10/1957 | Kazenas | 524/597 X |
| 4,059,407 | 11/1977 | Hochstrasser | 435/14 |
| 4,108,972 | 8/1978 | Dreyer | 436/800 X |
| 4,216,245 | 8/1980 | Johnson | 427/2 |
| 4,358,535 | 11/1982 | Falkor et al. | 435/5 |
| 4,385,126 | 5/1983 | Chen | 436/800 X |
| 4,496,658 | 1/1985 | Kondo et al. | 436/800 X |

OTHER PUBLICATIONS

Voedisch, R. "Luminescent Pigments, Organic", In Pigment Handbook (Patten, ed.) 1973, pp. 891–901.

*Primary Examiner*—Amelia Burgess Yarbrough
*Attorney, Agent, or Firm*—Joseph E. Mueth

[57] ABSTRACT

A general method of assay for biological molecules using daylight fluorescent particles. The method described is applicable to assays involving immunological reagents, nucleic acids, hormones and neurotransmitters.

13 Claims, No Drawings

USE OF DAYLIGHT FLUORESCENT PIGMENTS FOR TAGGING BIOLOGICAL MOLECULES

This is a divisional of co-pending application Ser. No. 07/262,184 filed on 10/20/88.

BACKGROUND OF THE INVENTION

The present invention relates to the use of daylight fluorescent materials as labels for biological molecules. More specifically this invention involves the use of daylight fluorescent materials in assays for antigens, antibodies, receptors, and fragments of nucleic acid macromolecules with particular base sequences.

Living organisms produce a variety of macromolecules with the unusual property of reversible binding to a highly restricted group of other molecules. The bonds formed are of intermediate strength, involving hydrogen bonds, Van der Waals forces and hydrophobic interactions.

Recognition is a term which has been used to describe this general phenomenon. Recognition is utilized widely by the immune system. Receptors on the surfaces of somatic cells recognize the presence of minute quantities of hormones; receptors on neurons and muscle cells recognize neurotransmitters in tissue fluids. Interaction of complementary strands of nucleic acids and of enzymes and their substrates are further examples of this general phenomenon.

Increasingly, recognition has become the preferred method of detecting specific biological molecules for scientific and clinical applications. The specificity and sensitivity of these reactions is very high.

The most common method for detecting biological recognition is to label one of the reacting species with a radioactive isotope as in radioimmunoassays (RIA). This method is effective and is used widely, especially in research laboratories which have the specialized equipment for use and detection of radioisotopes. The health hazard and expense involved in the use of radioisotopes, however, have limited use of the method outside of the research laboratory.

One alternative to the use of radioisotopes as labels is to covalently bind certain enzymes capable of generating a colored species from a colorless substrate to one of the reacting molecules. Although methods involving enzyme labels are very sensitive, time, temperature, and other conditions must be scrupulously controlled in order to achieve accurate results. In addition, enzymes are prone to denaturation and degradation during storage.

Fluorescent labels provide a third alternative and are not subject to the above described limitations. With sophisticated equipment, very high sensitivity can be achieved (U.S. Pat. No. 4,261,968). But fluorescent labels are subject to bleaching over time and under ordinary conditions of measurement.

Therefore despite the advantages of existing methods of assay involving fluorescent labels, there is a need for simpler assay methods. This is particularly true where the assay is to be conducted in an environment where sophisticated instrumentation is unavailable, such as small clinics, the farm or the home. Accordingly, it is desirable to develop assay methods utilizing fluorescent labels which do not require the specialized light sources or detectors otherwise used in such assays. Ideally it is desirable to achieve quantitative or semi-quantitative results using conventional light sources and the unaided eye, in a manner analogous to the use of pH paper.

SUMMARY OF THE INVENTION

It has now been discovered that biological macromolecules labeled with particles exhibiting the property of daylight fluorescence fulfill the needs described above. These labels fluoresce in response to wavelengths contained in ordinary indoor light as well as sunlight. In addition they reflect a portion of the incident light in the same approximate wavelength as fluorescent emission occurs. Accordingly, the luminance of such pigments is greater than either fluorescence or ordinary reflective pigments. As an example, the luminance of a typical daylight fluorescent orange is approximately 55 percent of incident illumination, whereas a nonfluorescent pigment of the same color has a luminance of only approximately 15 percent (Voedisch, "Luminescent Pigments, Organic" in *Pigment Handbook* at 898 (Patten, ed. 1973)). Labels of this type are stable even under brilliant illumination, unlike ordinary fluorescent pigments.

Materials exhibiting the property of daylight fluorescence are available in a variety of sizes including particles with molecular dimensions. Together with their high luminance and resistance to bleaching, daylight fluorescent particles have properties which have made it possible to devise, not only extremely sensitive and simple methods of instrumental analysis, but have permitted the development of assays that can be carried out with the naked eye using ordinary illumination. The latter development opens up the possibility of performing sensitive assays at low cost in the home, farm, and clinical office environment.

DETAILED DESCRIPTION

Methods for preparing daylight fluorescent materials have been known for over 30 years (Luminescent Pigments, supra at 896). Briefly, the property of daylight fluorescence is achieved by creating a dilute solution of certain dyes, such as rhodamine, in a solid phase. A dilute solution is required in order to avoid quenching of the fluorescence emission. There are three methods for achieving the desired dispersion in a solid phase. The dye may be mixed with a resin matrix which is subsequently dried and ground to a powder (U.S. Pat. No. 2,809,954). Alternatively, the powdered resin may be colored in a dye bath (U.S. Pat. No. 2,938,873) or a resin precipitate may be formed in a dye bath (British Pat. No. 770,889, cited in Luminescent Pigments, supra at p. 899). Powders prepared according to these methods are readily available from commercial sources.

In order to achieve consistent results with the techniques described below, it is desirable to utilize dye particles of uniform size. To this end, commercially prepared powders are obtained which have been prepared to contain predominantly particles of the desired size. These may be further fractionated by commercial firms which provide particle fractionation services. Alternatively they are fractionated in aqueous suspension by conventional differential centrifugation. Extremely small particles are fractionated by means of gel permeation chromatography.

The second step in preparing daylight fluorescent materials for assays involves binding them to molecules which are to be used in the desired assay. Since the recognition-based assays considered here involve binding of the fluorescent molecules to be detected by molecules complementary to them, the molecules complementary to those which are to be detected are linked to the fluorescent particles.

There are two general approaches to bonding biochemicals, including macromolecules to small polymeric particles. First, many molecules such as antibodies simply bind to hydophobic surfaces by non-covalent forces. In one example, monoclonal antibodies in 0.1 normal sodium chloride solution are mixed with daylight fluorescent particles and allowed to stand in a cold room for one hour. Excess antibody is used to insure complete coating of the microparticles. This excess is removed by repeated centrifugation and washing of the particles by filtration through microporous filters which pass the antibody but not the particles. Separation may be effected by gel permeation chromotography. This approach is simple and often is adequate.

A second and generally more desirable approach involves covalent bonding of the compounds to particles. In general it is desirable to first add a chemical moiety which forms an "extension arm" to the microparticle surface before bonding any other species thereto. Di-aminoheptane and/or partially polymerized glutaraldehyde are added to the particles prior to attaching the biochemical of interest, in this method. This provides easier assess to the biochemical of interest by functional groups involved in these specific reactions. Several types of daylight fluorescent microparticles are available which contain hydroxyl or carboxyl groups on their surfaces.

In an example, di-aminoheptane or epsilon-aminocaproic acid were bonded to microparticles using the aqueous carbodiimide reaction. See Molday, Dreyer, Rembaum and Yen, J. Cell. Biol., 64:75–88 (1975). After the coupling reaction was complete, excess reagents were removed by dialysis against 0.1 molar sodium cloride. Any of the biological probes discussed may then be easily bonded to these moieties using methods described below.

Many molecules which display specific recognition properties have primary amino groups available which can be used to couple these molecules to reactive microparticles. Almost all proteins and peptides can be bonded by means of such amino groups. Nucleic acid probes can now be automatically synthesized with one or more primary amino groups incorporated at the end of the polynucleotide sequence.

One convenient and effective means for coupling such molecules to microparticles which also have exposed primary amino groups involves the use of the bifunctional reagent glutaraldehyde, Molday et al., supra., and Rembaum, Yen, Cheong, Wallace, Molday, Gordon, and Dreyer, Macromolecules, 9:328–336 (1976). Briefly, an aqueous glutaraldehyde solution is added slowly to a suspension of microparticles in 0.1 molar sodium phosphate buffer at pH 7.0. The final concentration of glutaraldehyde was 1.25%. Reaction time at 25° C. is one hour after which excess glutaraldehyde was removed by efficient overnight dialysis at 4° C. against 0.1 molar sodium chloride in the same phosphate buffer as above. In a second step an excess of the biochemical compound (e.g., monoclonal antibody or DNA probe containing a primary amino group) is reacted with the glutaraldehyde activated microparticles for five hours at 25° C. In some experiments a longer reaction time and higher pH yields superior coupling. The excess reactants are removed by repeated centrifugation and washing with the phosphate buffered saline, at pH 7.0. Alternative methods for removing the excess reagents have already been discussed.

In some applications it is desirable to use partially polymerized glutaraldehyde rather than freshly purified monomers since this provides a longer molecular arm on the microparticles and access to the complementary target molecules is thereby increased.

There are numerous alternative methods for chemically bonding biochemical compounds to polymeric materials.

It should be emphasized that the scope of this invention includes all uses of daylight fluorescent molecules to detect biological molecules. It bears emphasis that this includes the use of daylight fluorescent materials in any reaction wherein a molecule to be detected originates in a living organism or such a molecule is used to detect another molecule. For example, antibody molecules can be used to detect a variety of molecules of synthetic origin (Fudenberg, Sites, Caldwell and Wells, *Basic and Clinical Immunology* (1976)), as well as molecules generated by living organisms. Synthetic DNA probes may be used to detect specific sequences of natural DNA.

Although in this discussion and in the examples that follow the terms antigen and antibody have been used, these terms are unduly restrictive. An antibody can be recognized as an antigen by another antibody. Also, in an assay system, an antibody can be detected by allowing it to bind to a molecule which is antigenic for it and which is immobilized on the surface of a microparticle. In order to discuss the present invention in the most general terms, the term immunological ligand will be used as a substitute for antigen and antibody.

The assays described below are adaptable to the detection of hormones, neurotransmitters and their receptors, as well as for nucleic acid strands containing particular coding sequences.

Example 1

A pattern of small blind holes or wells, each several millimeters in diameter, are machined or molded into one end of a small plastic dipstick. A different immunological ligand (or a different concentration of such ligand) is then bonded to the bottom of each small well using methods already described for bonding biochemical compounds to polymers. The stick is then dipped into suitably diluted human serum which is thought to contain antibodies directed against one or more of the antigens now present in different wells of the dipstick. After a suitable reaction period which is normally 5 or 10 minutes, the dipstick is removed and excess serum is washed off. If the human serum being tested contained immunological ligands directed against any one of the immunological ligands present in the wells of the dipstick, those wells will now be coated with human immunological ligands. Purified goat antibodies, specific for human antibodies, are labeled with daylight fluorescent polymers, and are allowed to react with each of the wells on the dipstick. Again, after a suitable reaction time of 5 or 10 minutes, the excess reagent is washed away and the stick is examined for the presence of intense daylight fluorescence in any of the wells. In a test of this type it is often possible and satisfactory simply to examine the stick with the eye and note which wells are colored. This then indicates the presence of antibodies in the serum which are directed against the antigens of interest.

Example 2

A dipstick prepared as in Example 1 in which a series of wells are coated with different concentration of an immunological ligand, and a semi-quantitative result is obtained by noting each color in the well as compared with a reference.

Example 3

A dipstick prepared as in Example 1 and in which each of the wells is precoated with a pigment of different color than that attached to the second immunological ligand. Thus yellow wells change to various shades of orange or red when red daylight fluorescent labels are bound. A semi-quantitative indication of the concentration of molecules in the test solution can be obtained by comparing the color of the wells with the color of a reference chart.

Ordinary fluorescent as well as daylight fluorescent pigments may be used as labels in this assay.

Example 4

Immunoabsorbant purified goat anti-human chorionic gonadotropin (HCG) is coated in the form of an alphanumeric symbol such as a plus sign on a small, round, plastic disc. A preferred form of the disc is a macroporous, honeycomb or convoluted surface which has a greatly increased surface area. In one preferred form of this test the remainder of the disc surrounding the plus sign is coated with goat antibody which is not reactive with HCG. In order to detect the presence of HCG (i.e., a pregnancy test) the disc is allowed to react with a sample of human urine or serum. The disc is also allowed to react with a monoclonal antibody labeled with daylight fluorescent polymers, and which is directed against the beta chain of HCG. This reaction can either occur simultaneously with the incubation with the urine or serum, or in a subsequent step. The HCG serves as a bridge, binding the daylight fluorescent label to the surface of the plastic disc. After the excess reagent is rinsed away, the disc is examined under ordinary light or filtered light of the appropriate wavelengths. In many cases, UV light can also be used. If a colored-plus sign is seen, this indicates the presence of HCG in the sample tested. If no daylight fluorescence is seen, no HCG was present in the amount measurable by the assay. On the other hand, if the disc is completely colored, a false positive reaction is indicated because the region outside the plus sign was coated with the nonreactive goat antibody control. This new type of pregnancy test greatly minimizes one of the most serious difficulties normally encountered in pregnancy tests, namely false positive results in a finite percentage of the cases. It also reduces the subjective judgment needed in detecting a positive or negative result since a pattern (such as a plus sign) is present only in the case of a true positive reaction.

A variety of pigments, including ordinary fluorescent ones, chemiluminescent and electroluminescent pigments, and phosphorescent pigments may be used as labels in place of daylight fluorescent pigments.

Example 5

A honeycomb sponge or other high surface area material is contained within a cartridge capable of holding a test solution. Immunological ligands which bind the molecule to be assayed are bound to the surface of the material in the cartridge. These ligands are then saturated with a purified sample of the molecule to be assayed, or its analog. In either case the molecule used to saturate the binding sites is covalently bound to fluorescent particles. This sponge or honeycomb is then thoroughly washed and then dried in the presence of preserving material such as dilute glycerol or polymeric compounds which are utilized to stabilize the reagent. The honeycomb or sponge-like cartridge is used to absorb the test specimen which fills the volume of the cartridge. If the test sample contains the molecule sought it competes for the binding sites occupied by fluorescent labeled molecules. Thus when the sponge is exposed to the test solution the molecules sought to be assayed will compete for the binding sites on the sponge and cause the daylight fluorescent labeled particles to be free in solution. At the end of reaction period the labeled reagents which have been freed by reaction with the test solution are eluted from the cartridge and read quantitatively in a simple instrument which monitors the fluorescence emission.

Example 6

An assay as described in Example 5 where the material covalently bound to the sponge or honeycomb is a nucleic acid strand complementary to the nucleic acid sought to be assayed, and in which these sites are preabsorbed with nucleic acid strands similar or identical in base sequence to those sought to be assayed, and are covalently bound to a daylight fluorescent material.

Although six specific embodiments of the present invention have been presented in detail, other alternatives will be apparent to one skilled in this art. Accordingly, the embodiments discussed should be viewed as examples of the claimed invention rather than limitations.

What is claimed is:

1. A composition for use in assaying first biological molecules, comprising a plurality of microparticles exhibiting daylight fluorescence bound to second molecules complementary to those being assayed.

2. A composition according to claim 1 where the first and second molecules are immunological ligands.

3. A composition according to claim 1 where the first and second molecules are complementary strands of nucleic acids.

4. A composition for use in assaying of biological molecules including:
   (a) a plurality of first molecules complementary to second molecules to be assayed, said second molecules being said biological molecules; and
   (b) pigmented daylight fluorescent microparticles coated with third molecules also complementary to the second molecules.

5. A composition according to claim 4 wherein said second molecules are human chorionic gonadotropin.

6. A composition according to claim 4 in which microparticles exhibiting daylight fluorescence are bound to molecules complementary to molecules present on the surfaces of the labeled cells.

7. A composition according to claim 4 in which the complementary molecules are immunological ligands.

8. A composition for use in assaying biological molecules comprising a substrate to which are bound first molecules complementary to second molecules on a portion of the surface of said substrate, said second molecules being said biological molecules, the balance of the surface of said substrate having bound thereto third molecules, similar to the first molecules, but not complementary to the second molecules, and fourth molecules, also complementary to the second molecules and labeled with a daylight fluorescent pigment.

9. A composition according to claim 8 wherein said second molecules are human choronic gonatropin.

10. A composition according to claim 8 wherein the substrate is a convoluted surface.

11. A composition according to claim 8 wherein the complementary molecule is an immunological ligand.

12. A composition according to claim 8 wherein the complementary molecule is a nucleic acid.

13. A composition for use in assaying of biological molecules including:

(a) a plurality of first molecules complementary to second molecules to be assayed, said second molecules being said biological molecules, the first molecules being bound to the surface of a convoluted substrate in a container;

(b) the binding sites of the first molecules are saturated with third molecules which are the second molecules or analogues thereof; and (c) the third molecules are covalently bound to the surfaces of daylight fluorescent pigmented microparticles.

* * * * *

UNITED STATES PATENT AND TRADEMARK OFFICE
CERTIFICATE OF CORRECTION

PATENT NO. : 5,075,215
DATED : December 24, 1991
INVENTOR(S) : William J. Dreyer It is certified that error appears in the above-indentified patent and that said Letters Patent is hereby corrected as shown below:

On the title page: Item [62]:

- After Oct. 20, 1988, please add --, which was a a continuation of Patent Application Serial No. 134,587, filed December 15, 1987, which in turn was a continuation of Patent Application Serial No. 619,613, filed June 11, 1984.--

Signed and Sealed this

Thirty-first Day of August, 1993

*Attest:*

BRUCE LEHMAN

*Attesting Officer*  *Commissioner of Patents and Trademarks*